United States Patent [19]

McGrath et al.

[11] Patent Number: 4,664,097

[45] Date of Patent: May 12, 1987

[54] NUCLEAR TRANSPLANTATION IN THE MAMMALIAN EMBRYO BY MICROSURGERY AND CELL FUSION

[75] Inventors: James McGrath; Davor Solter, both of Philadelphia, Pa.

[73] Assignee: The Wistar Institute of Anatomy & Biology, Philadelphia, Pa.

[21] Appl. No.: 608,418

[22] Filed: May 9, 1984

[51] Int. Cl.$^4$ ...................... A61B 19/00; C12N 15/00; C12N 1/00

[52] U.S. Cl. .................................. 128/1 R; 435/172.3; 435/172.2; 435/317; 935/53; 935/111

[58] Field of Search .................. 435/172.3, 317, 172.2; 935/53, 111; 119/1; 128/1 R

[56] References Cited

PUBLICATIONS

McGrath et al., Science 220: 1300–2 (1983).
McGrath et al., Nature 308: 550–1 (1984).
McGrath et al., Cell 37: 179–183 (1984).
McGrath et al., Science 226: 1317–19 (1984).
Mann et al., Nature 310: 66–67 (1984).
Barton et al., Nature 311: 374–6 (1984).
Swani et al., Cell 45: 127–136 (1986).
Willadsen, Nature, 320: 63–65 (1986).
Hoppe, P. C. et al., Proc, Natl. Acad. Sci. USA, vol. 79, pp. 1912–1916 (1982).
Nature, vol. 303, p. 363 (Jun. 1983).
Lin, T. P. et al., Nature vol. 242 (Mar. 1983) pp. 47 and 48.
Modlinski, J. A., J. Embryol. Exp. Morph. vol. 66, pp. 153–161 (1980).
Illmensee, K. et al., Cell vol. 23 pp. 9–18 (Jan. 1981).
Soltes et al., Cold Spring Harbor Symposium on Quantitative Biology vol. L: 45–50 (1985).
Swani et al., Science 222: 1034–36 (1983).
Swani et al., Nature 308: 548–550 (1984).
McLanen, Nature 309: 671–2 (1984).

*Primary Examiner*—Alvin E. Tanenholtz
*Attorney, Agent, or Firm*—Howson and Howson

[57] ABSTRACT

Nuclear transplantation in the mouse embryo is achieved by using a method that combines microsurgical removal of the zygote pronuclei with the introduction of a donor nucleus by a virus-mediated cell fusion technique.

5 Claims, 4 Drawing Figures

NUCLEAR TRANSPLANTATION IN THE MAMMALIAN EMBRYO BY MICROSURGERY AND CELL FUSION

This invention relates to a novel microsurgical procedure designed to effect nuclear transplantation and cell fusion in mammalian embryos. The research work which resulted in the present invention was supported by grants from the National Cancer Institute, from the National Institute of Child Health and Human Development, and from the National Science Foundation.

BACKGROUND OF THE INVENTION

In recent years there has been considerable interest in determining the contributions to embryonic and adult phenotype by the pronuclei and cytoplasm of mammalian embryos. For example, hairpin-tail ($T^{hp}$) in mice is an allele of branchyury (T) situated on chromosome 17 (linkage group IX) of the mouse (Johnson, D. R., *Genetics* 76, 795–805 (1974)). It appears to differ from all previously described mammalian genes in that the phenotype and viability of the heterozygote depend upon the parent from which the $T^{hp}$ gene is inherited. Heterozygotes with a $T^{hp}/+$ father are short tailed and generally viable. On the other hand, the majority of the heterozygotes whose $T^{hp}$ was derived from the egg die in the latter half of embryogenesis (gestational days 15-16) with a few exceptional $T^{hp}/+$ embryos surviving until birth (Johnson, D. R. *Genet. Res.* 24, 207-213 (1975); Alton A. *Doctoral Dissertation*, Cornell U., N.Y. (1982). Those $T^{hp}/+$ progeny born, however, are cyanotic and die within 24 hours of parturition (Johnson, D. R. (1975), supra.). The $T^{hp}$ maternal lethal effect transmitted through the ovium could be inherited via the cytoplasm (oogenic defect) or via the female pronucleous (embryogenic defect). Thus, a method for determining whether this defect is transmitted by the pronucleus or cytomplasm of the egg would be most useful.

Another problem is that of breeding barriers. There are several different species of mice. Some can interbreed, while others cannot. The breeding barrier is caused by the plasma membrane and cytoplasm of the embryo. Accordingly, it would be desirable to provide a method whereby the breeding barrier could be overcome.

Another area of concern is the potential extinction of certain rare mammalian species, an example of which is the Siberian tiger. There are very few of this species remaining and their reproductive performance is poor. Accordingly it would be desirable if a method could be devised whereby such species could be preserved.

It would also be desirable to develop certain mammalian strains having desirable genetic characteristics provided by the pronucleus of one genotype and those provided by the cytoplasm of another genotype.

Nuclear trannsplantation methods might provide a viable solution to the foregoing problems. Nuclear transplantation studies in the amphibian embryo have provided valuable information about the possible restriction of nuclear potential during development (Danielli, J. R., et al, *Int. Rev. Cytol.* Suppl. 9 (1979)). Similar experiments in the mammalian embryo have been hindered by the small size of the embryo and its sensitivity to microsurgical manipulation. Although some success in nuclear transplantation in the mouse embryo by microsurgery has been reported (Illmensee K. et al, *Cell* 23 9–18 (1981)), it is believed to be due to the fact that the enucleation of the recipient cell in a small number of cases was incomplete enabling growth.

SUMMARY OF THE INVENTION

This invention relates to a novel microsurgical method for nuclear transplantation in mammilian embryos which, in its most fundamental aspects comprises:

(a) penetrating the zona pellucida of a one-cell stage mammalian donor embryo with an enucleation pipette without penetrating the plasma membrane of the donor embryo, the pipette having an internal diameter sufficiently large to receive the pronuclei of the donor embryo without rupturing same;

(b) aspirating a small portion of the plasma membrane and cytoplasm and pronuclei of the door embryo into the pipette with the plasma membrane surrounding the pronuclei;

(c) withdrawing the pipette from the donor embryo to cause the plasma membrane extending between the pipette and donor embryo to form a fine thread and the orifice made by the pipette in the zona pellucida to close and pinch off the plasma membrane at the site of the orifice;

(d) introducing the pipette containing the membrane-bound pronuclei to a liquid suspension of inactivated Sendai virus and aspirating into the pipette a small quantity of the virus suspension;

(e) penetrating the zona pellucida of a recipient mammalian embryo which has been enucleated by the procedure of steps (a), (b) and (c) at the site of enucleation without penetrating the plasma membrane, and injecting the virus suspension and membrane-bound pronuclei into the perivitelline space of the recipient embryo;

(f) withdrawing the pipette from the recipient embryo, and (g) incubating the recipient embryo at about 37° C. for a period of time to effect fusion of the pronuclei with the recipient embryo.

The recipient embryo containing membrane-bound nuclei is incubated for a period of time to permit the embryo to develop to the blastocyst stage, and then transferred to the uterus of a pseudopregnant mammal. Prior to being enucleated, the embryos should be placed in Hepes-buffered Whitten medium containing cytochalasin B and Colcemid.

The above-described microsurgical procedure advantageously provides an elegant tool for investigating solutions for the above discussed problems. More particularly, the method has been used successfully to investigate the nuclear/cytoplasmic origin of maternal $T^{hp}$ lethality in the mouse by using it in performing reciprocal nuclear transplantation between one cell stage embryos from $T^{hp}/+$ and $+/+$ females. The results obtained show that the introduction of $T^{hp}/+$ pronuclei into $+/+$ cytoplasm does not reverse the maternally inherited lethal effect of $T^{hp}$ and leads to the conclusion that in the fertilized egg, the defect responsible for the $T^{hp}/+$ maternal lethal effect lies in the pronuclei and not in the egg cytoplasm.

The microsurgical technique of the present invention may also be adapted to overcoming the breeding barrier problem. For instance, the embryo for one species could be enucleated and the pronuclei from another species could be introduced to the enucleated embryo, followed by incubation and cell fusion. After development to the blastocyst stage, the embryo may then be transferred to the uterus of a pseudo-pregnant female of the species which produced the recipient embryo.

A procedure similar to that indicated for overcoming the breeding barrier problem may be used in preserving a rare mammalian species. Thus, the pronuclei from the embryo of a Siberian tiger could be introduced into the enucleated embryo of a common lion species. After incubation the embryo could then be transferred to the uterus of a psudo-pregnant female of the same species which produced the recipient embryo.

The present invention also makes possible the development of certain mammalian strains having the desirable genetic characteristics provided by the pronucleus of one genotype and those provided by the cytoplasm of another genotype.

The foregoing advantages as well as others of the invention will become further apparent from the following detailed description, appended claims and drawings in which:

Figure 3:
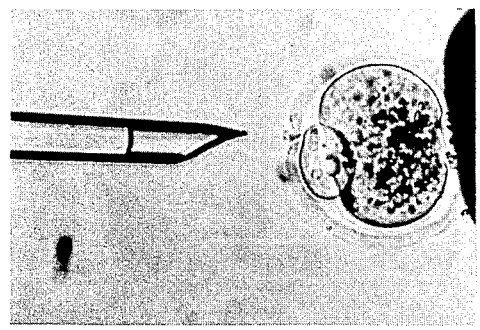
Figure 4:
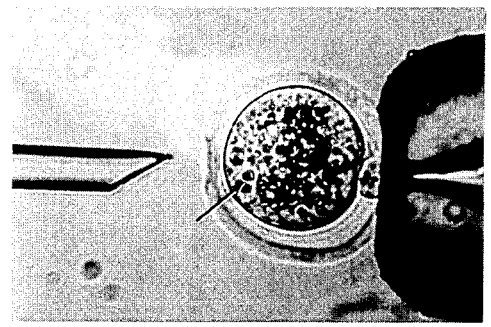

FIG. 3 is a further photomicrograph showing an enucleated mouse embryo of a different strain secured by a holding pipette, the zona pellucida having been penetrated by the enucleation pipette containing the pronucleus and inactivated Sendai virus at the site of enucleation and the pronuclei and Sendai virus having been injected into the perivitelline space, and FIG. 4 is a photomicrograph of the embryo of FIG. 3 showing that fusion of the pronuclear karyoplast with the enucleated embryo has taken place.

DETAILED DESCRIPTION OF THE INVENTION

Although the detailed description of the invention is with respect to nuclear transplantation and cell fusion in the mouse embryo, it will be readily apparent to those skilled in the art that the microsurgical procedure described is applicable to other mammalian species.

The holding and enucleation pipettes for use in the novel microsurgical process can be fashioned from Pyrex capillary tubing of suitable size which can, if necessary be drawn to a size related to the size of the embryos and pronuclei. In the case of mouse embryos the tubing from which the enucleation pipette is fashioned can have an outer diameter of about 1.0 mm and an inner diameter of about 0.65 mm. Using a standard pipette puller, e.g. a DKI vertical puller, the outer diameter can draw down to about 15 to 20 $\mu$m. The inside diameter of the pipette after drawing should be sufficient to enable aspiration of the pronuclei and surrounding plasma membrane into the pipette without injuring the pronuclei or rupturing the plasma membrane. The tip of the enucleation pipette should be beveled and the outermost portion of the bevel should be provided with a longitudinally extending tip to enable piercing of the zona pellucida (see the several figures). The bevel can be obtained on a grinding wheel, followed by treatment of the bevel with a solution of hydrofluoric acid (25 percent) and sharpening on a microforge.

The holding pipettes may be fashioned from the same Pyrex capillary tubing as the enucleation pipette. The holding pipette usually can be hand-drawn over a burner to the desired size, e.g. 75 to 100 $\mu$m for securing a mouse embryo. The end which comes in contact with the embryo should be rounded and polished (see FIGS. 2 and 4).

Before use, the pipettes should be cleaned and sterilized.

One cell stage embryos are obtained from oviducts excised from spontaneoulsy mated females on the day of vaginal plug (usually day 1). Cumulus cells can be dispersed in Whitten medium (Whitten, W. K., *Adv. Biosci.* 6, 129 (1971)) containing bovine hyaluronidase (500 non-filtered units per ml.). Before microsurgery, the embryo, usually a group of six to eight embryos, is incubated for 10 to 45 minutes at 37° C. in an atmosphere of 5 percent $O_2$, 5 percent $CO_2$ and 90 percent $N_2$ in bicarbonate-buffered Whitten medium containing cytochalasin B (5 $\mu$g/ml) and Colcemid (0.1 $\mu$g/ml) (McGrath, J. and Solter, D., *Science* 220 1300 (1983). The cytochalasin B destroys reversibly the microfilaments in the embryo and the Colcemid destroys the microtubules. As a result of such treatment the embryo is quite flexible. Each embryo is then placed singly in a hanging drop of Hepes-buffered Whitten medium containing cytochalasin B (5 $\mu$g/ml) and Colcemid (0.1 $\mu$g/ml) in a Leitz or other suitable microscope oil chamber fitted with a micromanipulators and a fixed stage microscope such as a Leitz Laborlux II. All microsurgery is performed as described in greater detail hereinbelow.

Sendai virus used in the microsurgical procedure of the invention may be obtained from the infected allantoic fluid of embryonated chicken eggs and inactivated with $\beta$-propiolactone at a concentration of 2000 to 3000 hemaglutinating units per millimeter (Giles, R. E. et al, *In Vitro* 9 103 (1973); Neff, J. M. et al, *Prac. Soc. Exp. Biol. Med* 127 206 (1968); Graham, C. F., *Acta Endiocrinol. Suppl.* 153, 154 (1971). The Sendai virus is a flu-type virus which has been inactivated, but has intact proteins, and causes cell fusion.

Following the microsurgery, the recipient embryo is washed one or more times and cultured to the blastocyst stage in 50 $\mu$l drops of modified Whitten medium (Abramczuk, J., et al., *Dev. Biol.* 61, 378 (1977)) under silicone oil at 37° C. in an atmosphere of 5 percent $O_2$, 5 percent $CO_2$ and 90 percent $N_2$ (*Nature (London)* 283) 479 (1980)).

The embryo at the blastocyst stage may be transferred to the uterus of a pseudopregnant female. Also control embryos isolated at the one-cell stage are similarly cultured and transferred to the uteri of pseudopregnant females. However, the control embryos are not exposed to cytoskeletal inhibitors or inactivated Sendai virus.

Turning now to the microsurgical procedure of the invention, the mouse embryos are incubated before and during microsurgery in cytochalasin B (Ilmensee, K. et al, *Cell* 23, 9 (1981); Hoppe, P. C., et al, *Proc. Natl. Acad. Sci., U.S.A.* 79, 1012 (1982) and 74, 5657 (1977); Modlinski, J. A., *J. Embroyl. Exp. Morphol.* 60 153 (1980)) and Colcemid. Each embryo is then secured by a holding pipette and the zona pellucida is penetrated with an unucleation pipette of the type heretofore described. Penetration of the plasma membrane, however, is avoided and the pipette is advanced to a position adjacent each pronucleus. Upon aspiration, a small portion of the plasma membrane and surrounding cytoplasum are drawn into the pipette, followed by the pronucleus.

The pipette containing the entire pronucleus is then moved to a point adjacent the second pronucleus and the latter is similarly aspirated.

Figure 1:
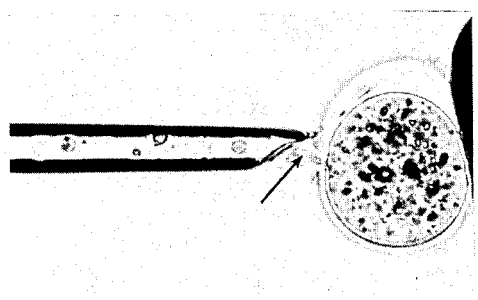
FIG. 1 is a photomicrograph showing a mouse embryo secured by a holding pipette, the zona pellucida having previously been penetrated with an enucleation pipette, and the pronuclei having been aspirated into the pipette.
Figure 2:
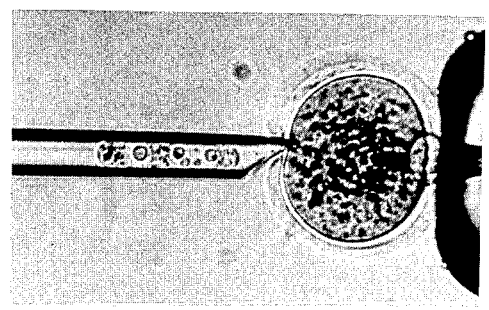
FIG. 2 is a photomicrograph of the same embryo as FIG. 1, but showing the enucleation pipette containing the pronuclei withdrawn from the embryo and a bridge of plasma membrane extending from the embryo through the zona pellucida and into the pipette.

Referring to FIG. 1, as the enucleation pipette is withdrawn, the plasma membrane which extends into the pipette and surrounds the pronuclei stretches into a fine thread or cytoplasmic bridge which is then pinched off by the zona pellucida through closing of the orifice made by the pipette therein (see arrow FIG. 1 and FIG. 2).

The pipette, which contains the membrane-bound pronuclei (pronuclear karyoplast), is moved in contact with the Sendai virus suspension, described previously, and a small volume of the virus suspension, generally on the order of the volume of the pronuclear kyroplast, is aspirated into the pipette.

The pipette containing both the pronuclear kyroplast and Sendai virus is moved to a third drop containing an embryo enucleated previously using the above-described procedure. The zona pellucida of the latter embryo is penetrated at the previous site of enucleation, and the virus suspension and pronuclear karyoplast are injected into the perivitelline space (see FIG. 3). After withdrawal of the pipette, the embryo is incubated at 37° C. Fusion of the pronuclear karyoplast with the enucleated embryo generally occurs during the first hour of incubation (see FIG. 4).

The embryo is then cultured in vitro for approximately 5 days during which the embryo develops into the blastocyst stage. The embryo is then transferred to the uterus of a pseudopregnant female where gestation takes place resulting in the birth of a progeny. Alternatively the manipulated embryo is transferred to the oviduct of a pseudopregnant female immediately after the nuclear tranfer (McGrath, J. and Solter, D., *Nature* (*London*) 308 550 (1984).

A study was made to determine the efficiency of the nuclear transplant procedure described above. The study involved a total of 73 embryos divided among three different mouse genotypes. The results of the study are set forth in Table 1, below:

TABLE 1

Efficiency of the Nuclear Transplatation Technique

| Genotype | Enucleation[1] | Karyoplast Injection[2] | Fusion[3] |
|---|---|---|---|
| C3H/HeJ | 24 of 26 | 24 of 24 | 23 of 24 |
| C57BL/6J | 35 of 35 | 34 of 35 | 34 of 34 |
| ICR | 11 of 12 | 10 of 11 | 10 of 10 |
| Total (%) | 70 of 73 (96) | 68 of 70 (97) | 67 of 68 (99) |

[1]Number of embryos surviving microsurgical removal of both male and female pronuclei per total number of embryos.
[2]Number of pronuclear karyoplasts surviving injection into the perivitelline space of the recipient embryo per total number of karyoplasts injected.
[3]Number of pronuclear karyoplasts fusing with the recipient embryo per total number of karyoplast-injected embryos.

Referring to Table 1, it can be seen that of 73 experimental embryos, 70 (96%) were successfully enucleated, and of the 70 pronuclear karyoplasts obtained, 68 (97%) were successfully introduced (with Sendai virus) into the perivitelline space of enucleated zygotes. After incubation at 37° C., 67 (99%) of these karyoplasts fused to the plasma membrane of the ovium. The overall efficiency of the transplantation method of the invention was, therfore, 91 percent.

After microsurgery, experimental and control embryos were cultured for 5 days and the number of embryos successfully developing to the bastocyst stage was determined. Of 34 control embryos, all developed to the morula or bastocyst stage (Table 2). Similarly, of the 67 experimental embryos, 64 (96%) developed to the morula or blastocyst stage. Transfer of the 34 control embryos to the uteri of pseudopregnant females resulted in the birth of five progeny (15%), three of which survived to adulthood. Transfer of the 64 experimental embryos to the uteri of pseudopregnant females resulted in the birth of ten progeny (16%), seven survived to adulthood. These seven offspring all displayed the coat color phenotype of the donor nuclei, and five were fertile.

Thus the technical manipulations involved in transferring pronuclei from one zygote to another did not significantly affect the ability of embryos to undergo normal development. The high frequency of developmental arrest in both experimental and control groups after the implantation procedure may have resulted from the in vitro culture period before implantation, since the intrauterine transfers of 22 carrier blastocytsts that had developed in vivo resulted in the birth of 17 progeny. Reciprocal pronuclear transplantations between genetically distinct one-celled embryos may be used to define the degree to which maternally inherited cytoplasmic components persist.

TABLE 2

Development of Control and Nuclear-Transplant Embryos. The Subscripts n and c Refer to the Strain Origin of the Nucleus and the Cytoplasm, respectively.

| | Developmental stage by day 5 in vitro (number of embryos) | | | |
|---|---|---|---|---|
| Group and Strain | Arrested | Morula | Blastocyst | Number Born[4] |
| Control | | | | |
| C3H/HeJ | 0 | 3 | 11 | 0 |
| C57BL/6J | 0 | 1 | 13 | 4 |
| ICR | 0 | 1 | 5 | 1 |
| Total | 0 | 5 | 29 | 5 |
| Nuclear-transplant | | | | |
| C3H/He$_n$ to C57B1/6J$_c$ | 0 | 0 | 23 | 4 |
| C57BL/6J$_n$ to C3H/He$_c$ | 0 | 1 | 23 | 3 |
| ICR$_n$ to C57BL/6J$_c$ | 1 | 0 | 9 | 2 |
| C57B/6J$_n$ to ICR$_c$ | 2 | 0 | 8 | 1 |
| Total | 3 | 1 | 63 | 10 |

[4]Number of offspring born after transfer of morulae and blastocysts into the uteri of females of the third day of pseudopregnancy.

The microsurgical procedure of this invention was also used in a study to determine whether $T^{hp}$ lethality in the mouse is a nuclear of a cytoplasmic defect.

Using the microsurgical procedure of this invention, one cell-stage embryos obtained from $+/+$ albino females mated to $+/+$ albino males were used in reciprocal nuclear transplantations with one cell-stage embryos obtained from pigmented $T^{hp}/+$ females previously mated to pigmented $+/+$ males. Nuclear transplant embryos were transferred to the oviducts of day 1 pseudopregnant females and allowed to develop to term. The number, coat color phenotype and tail length of the progeny were observed as $T^{hp}$ causes a shortening of the tail when heterozygous.

$T^{hp}/+$ embryos were obtained from brown or agouti $T^{hp}/+$ females mated to C57BL/6J males, while $+/+$ embryos were obtained from matings of outbred albino CD-1 (Charles River) males and females. Pseudopregnant females were obtained from matings of CD-1 females with vasectomized and proven sterile CD-1 males. All matings were spontaneous. Female mice were sacrificed on the day of vaginal plug detection (day 1 of pregency) and their oviducts excised. The ampulla of the oviduct was punctured with a watchmaker forceps and the released embryos were freed from surrounding cumulus cells by incubation in modified Whitten's medium (Whitten, W. K. supra.) containing 500 u/ml bovine hyaluronidase (Sigma). Nuclear transplatation was performed as previously described. Among 545 embryos, 535 (96%) were successfully enucleated and of the 524 pronuclear karyoplasts, 494 (94%) were successfully injected along with inactivated Senda virus into the perivitelline space of enucleated recipient embryos. 403 (~80%) of the pronuclear karyoplast: enucleated cytoplasm pairs underwent fusion. The latter were transferred on the day of microsurgery to the oviducts of day 1 pseudopregnant females using a small bore glass pipette. The results of these experiments are set forth in Table 3.

TABLE 3

Phenotype of Nuclear Transplant Offspring

| Nuclear genotype | Cytoplasmic genotype | No. of successful nuclear transplants | No. of progeny Normal Tail | No. of progeny Short Tail |
|---|---|---|---|---|
| $T^{hp}/+, +/+$ | $+/+$ | 206 | 16 | 2 |
| $+/+$ | $T^{hp}/+, +/+$ | 197 | 45 | 0 |

Referring to Table 3, of 197 successful nuclear transplant embryos in which wild-type pronuceli from albino females mated to albino males were introduced into the cytoplasm of enucleated embryos from pigmented $T^{hp}/+$ females, 45 (20 females and 25 males) normal-tailed albino progeny resulted (23%). Among 206 successful nuclear transplant embryos in which pronuclei from pigmented $T^{hp}/+$ females mated to pigmented males were introduced into the cytoplasm of enucleated embryos from albino females, 18 (10 females and 8 males) pigmented progeny were born (9%). Thus, a significantly greater proportion of nuclear transplant embryos, in which the egg cytoplasm was derived primarily from $T^{hp}/+$ females, developed to term (23%) than those embryos in which egg cytoplasm was derived primarily from $+/+$ females (9%) ($X^2 = 8.99$; $P < 0.01$). These data show no evidence that ovum cytoplasm from $T^{hp}/+$ females inhibits normal embryogenesis.

Since the $T^{hp}/+$ females were mated to $+/+$ males, half of the nuclear transplant embryos should be $T^{hp}/+$ (short-tailed) and half $+/+$ (normal-tailed). Among the 18 progeny which resulted from the introduction of pronuclei from $T^{hp}/+$ females into $+/+$ cytoplasm (Table 3), a significantly greater number of normal-tailed progeny were born (16) than short-tailed progeny (2) ($X^2 = 9.38$; $P < 0.01$). Of the 16 normal-tailed progeny, 2 were dead at birth while the remaining 14 were viable and survived to adulthood. Of the two $T^{hp}/+$ progeny, one was dead at birth while the other was edematous, cyanotic and died within 24 hours of parturition. The number of viable normal-tailed progeny (14) is significantly greater than the number of viable short-tailed progeny (0) ($X^2 = 12.06$; $P < 0.001$). Because the introduction of $T^{hp}/+$ pronuclei into wild-type cytoplasm did not result in the birth of viable $T^{hp}/+$ progeny it can be concluded that $T^{hp}$-lethality is inherited as a nuclear, not cytoplasmic, defect.

The several technical papers identified in this specification are incorporated by reference herein in their entirety.

We claim:

1. A microsurgical method for nuclear transplantation in non human mammalian embryos which comprises:

(a) penetrating the zona pellucida of a one-cell stage non human mammalian donor embryo with an enucleation pipette without penetrating the plasma membrane of said donor embryo, said pipette having an internal diameter sufficiently large to receive the pronuclei of said donor embryo without rupturing same;

(b) aspirating a small portion of said plasma membrane and cytoplasm and said pronuclei of said donor embryo into said pipette with said plasma membrane surrounding said pronuclei;

(c) withdrawing said pipette from said donor embryo to cause said plasma membrane extending between said pipette and donor embryo to form a fine thread and said orifice made by said pipette in said zone pellucida to close and pinch off said plasma membrane at the site of said orifice;

(d) introducing said pipette containing said membrane-bround pronuclei to a liquid suspension of inactivated Sendai virus and aspirating into said pipette a small quantity of said virus suspension;

(e) penetrating the zone pellucida of a recipient non human mammalian embryo which has been enucleated by the procedure of steps (a), (b) and (c) at the site of enucleation without penetrating the plasma membrane, and injecting said virus suspension and said membrane-bound pronuclei into the perivitelline space of said recipient embryo;

(f) withdrawing said pipette from said recipient embryo, and (g) incubating said recipient embryo at about 37° C. for a period of time to effect fusion of said pronuclei with said recipient embryo, said embryos being incubated prior to and during said microsurgery in cytochalasin B and Colcemid.

2. The method of claim 1 in which said recipient embryo containing membrane-bound nuclei is incubated for a period of time to permit said embryo to develop to the blastocyst stage.

3. The method of claim 2 in which said embryo at the blastocyst stage is transferred to the uterus of a pseudopregnant non human mammal.

4. The method of claim 1 in which said embryos are obtained from mice.

5. The method of claim 1 in which the pronucleic from the recipient embryo are introduced into the donor embryo.

* * * * *